United States Patent [19]

Gum et al.

[11] 4,273,937

[45] Jun. 16, 1981

[54] ORGANIC AMINE COMPOSITIONS

[75] Inventors: Mary L. Gum, Granite Springs; Nancye D. Kearns, Ossining, both of N.Y.

[73] Assignee: Union Carbide Corporation, New York, N.Y.

[21] Appl. No.: 105,243

[22] Filed: Dec. 19, 1979

[51] Int. Cl.³ .................... C07C 85/26; C07D 295/02; C07D 265/30; C07D 213/02
[52] U.S. Cl. .................................... 564/2; 260/313.1; 260/311.1; 260/326.8; 544/106; 544/358; 546/1; 546/184; 548/373; 548/379; 564/5
[58] Field of Search .................... 564/2, 5; 260/313.1; 548/373; 544/106; 546/1, 351

[56] References Cited

U.S. PATENT DOCUMENTS

| | | | |
|---|---|---|---|
| 4,079,153 | 3/1978 | Coleman | 426/266 |
| 4,087,561 | 5/1978 | Bharucha et al. | 426/266 |
| 4,088,793 | 5/1978 | Bharucha et al. | 426/266 |

OTHER PUBLICATIONS

Gray et al., "J. Food Sci.," vol. 40, pp. 981–984 (1975).

*Primary Examiner*—John Doll
*Attorney, Agent, or Firm*—Franklyn Schoenberg

[57] ABSTRACT

Organic amine compositions which are substantially free of nitrosamine contaminants are provided which comprise an organic amine and an inhibiting amount of an inhibitor additive selected from the group consisting of 1,4-naphthoquinone, 1,4-naphthohydroquinone, alkyl-derivatives of said quinones, and mixtures of the same.

13 Claims, No Drawings

ORGANIC AMINE COMPOSITIONS

BACKGROUND OF THE INVENTION

This invention relates to improved organic amine compositions and, more particularly, to organic amine compositions in which the formation of nitrosamine impurities is significantly reduced.

Organic amines have many diverse industrial applications having found wide use, both as a substantially 100 percent active composition and as aqueous solutions. Recently, N-nitrosamines, which are the reaction products of amines, and particularly secondary amines, with nitrosating agents have been found to be carcinogenic in tests on experimental animals and they are regarded as a potential hazard to humans. As a result, there has been a growing concern in recent years over their presence in products such as food, cosmetics, metal working compounds and the like.

Unfortunately, minute amounts of the undesirable nitrosamines have been found in various amines such as alkanolamines even though the nitrosating agent may not be apparent. It is desirable, therefore, to reduce, eliminate, or prevent the formation of nitrosamines in amine compositions and thereby eliminate this possible source of such contaminants in the many products in which the amines are used.

Heretofore, several approaches have been suggested for solving the nitrosamine contamination problem, particularly where known nitrosating agents such as inorganic nitrites are also present, for example, as food additives, corrosion inhibitors for aqueous solutions, etc. For example, in U.S. Pat. Nos. 4,087,561 and 4,088,793 to Bharucha et al. there is disclosed the use of 1,2,3,4-tetrahydro-6-alkoxy quinoline compounds or nitroxide derivatives of 1,2-dihydro and 1,2,3,4-tetrahydro-6-alkoxy quinoline compounds for reducing or eliminating the formation of undesirable nitrosamines during cooking of processed meat products containing nitrites, and Gray and Dugan, Jr. in Journal of Food Science, Vol. 40 (1975), pages 981–984, disclose the results of an evaluation of potential nitrosamine inhibitors including antioxidant compounds such as hydroquinone in acidic aqueous media and in low moisture carboxymethylcellulose systems. While such approaches have shown promise in inhibiting the formation of nitrosamines, the amounts of the inhibitors required are generally greater than would be desired and there can be found no suggestion that would appear to be directly applicable to the problem involved with eliminating or preventing the formation of nitrosamines in organic amines such as alkanolamines.

SUMMARY OF THE INVENTION

In accordance with the present invention there are provided organic amine compositions which are substantially free from undesirable nitrosamine impurities comprising an organic amine and a small inhibiting amount of a member selected from the group consisting of 1,4-naphthoquinone, 1,4-naphthohydroquinone, alkyl-substituted derivatives thereof, and mixtures of the same.

Also provided in accordance with the invention is a method for reducing or eliminating the formation of nitrosamine in compositions containing organic amines which comprises incorporating a small inhibiting amount of an inhibitor selected from the group consisting of 1,4-naphthoquinone, 1,4-naphthohydroquinone, alkyl-substituted derivatives thereof and mixtures of the same in said compositions.

It has been found that the organic amine compositions of the present invention including compositions containing alkanolamines and aqueous solutions thereof are substantially free of undesirable nitrosamine impurities, the formation of such impurities being significantly reduced or eliminated, even in the presence of a nitrosating agent, by the presence of a small inhibiting amount of the quinone derivatives herein described.

DESCRIPTION OF THE INVENTION

The organic amines to which the present invention is applicable are primary, secondary and tertiary monoamines including primary, secondary and tertiary aliphatic and cycloaliphatic amines such as, for example, methylamine, ethylamine, propylamine, butylamine, pentylamine, hexylamine, heptylamine, octylamine, nonylamine, decylamine, dodecylamine, tetradecylamine, octadecylamine, dimethylamine, dipropylamine, methylethylamine, diethylamine, dibutylamine, butylethylamine, diamylamine, dihexylamine, diheptylamine, dioctylamine, methyloctylamine, dinonylamine, didecylamine, didodecylamine, dinonylamine, trimethylamine, triethylamine, tripropylamine, trioctylamine, cyclohexylamine, dicyclohexylamine, cyclopentylamine, dicyclopentylamine, cycloheptylamine, dicycloheptylamine, methylcyclopentylamine, cyclooctylamine and ethylcyclooctylamine.

Also suitable are polyamines such as the alkylene diamines, for example, ethylene diamine, diethylene triamine, triethylene tetramine, propylene diamine, dipropylene triamine, heterocyclic amines such as pyrrole, pyrrolidine, piperazine, pyridine, morpholine, piperidine, pyrazole, pyrazoline, and indole.

Also suitable are the aromatic amines such as aniline and alkyl and halogen-substituted aromatic amines as well as N-substituted aromatic amines such as N-methyl aniline, N-ethyl aniline, N-diethyl aniline, p-anisidine and p-phenetidine.

Further applicable amines are organic compounds which contain both amino and hydroxyl groups including organic compounds which contain both amino and hydroxyl groups including, for example, monoethanolamine, N-methyl ethanolamine, N-ethyl ethanolamine, N-(n-propyl)ethanolamine, N-(isopropyl)ethanolamine, N-(n-butyl)ethanolamine, diethanolamine, N,N-di(n-propyl)ethanolamine, N,N-di(isopropyl)ehtanolamine, N,N-di(n-butyl)ethanolamine, N-methyl diethanolamine, triethanolamine, and mixtures thereof. Also suitable can be propanolamines such as monopropanolamine, dipropanolamine, tripropanolamine, and N-aminoethylethanolamine as well as the aminophenols such as p-aminophenol, m-aminophenol and o-aminophenol.

An essential component of the compositions of the invention is an inhibitor compound which is a member selected from the group consisting of 1,4-naphthoquinone, 1,4-naphthohydroquinone and alkyl derivatives thereof and mixtures of the same.

As a general rule, said quinones are used in an amount sufficient to significantly inhibit or reduce formation of nitrosamines in the amine compositions. The minimum amounts may vary somewhat depending upon the operating conditions and service requirements of the application in which the compositions are to be employed and may be readily determined by routine experimentation. The amount of said quinones that should be used will be termed herein as an "inhibiting amount" which is defined as being the minimum required to substantially reduce the formation of nitrosamines for a particular application. In general, however, the minimum "inhibiting amount" will be at least about one part per million of amine composition with amounts in the range of about 50 parts to about 150 parts per million being advantageously employed. The maximum amount of inhibitor that should be used is not critical with economic factors generally determining the use of amounts greatly in excess of that actually required.

The organic amine compositions of the invention can be used in their substantially 100 percent active form or as aqueous solutions thereof. The proportions of organic amines in such aqueous solutions is dependent upon the particular application for which they are intended and can be varied within a wide range to obtain the desired results.

The organic amine compositions of the invention can be prepared and, in accordance with the invention, the formation of nitrosamines in compositions containing organic amines can be inhibited by combining an "inhibiting amount" of a suitable quinone inhibiting compound as herein described with an organic amine compound or composition in any known suitable apparatus having mixing means that will conveniently form a uniform mixture, and preferably dissolve, said inhibitor compound in the amine or amine composition.

The compositions of this invention as well as the controls which demonstrate the prior art were evaluated in compositions containing high levels of sodium nitrite as nitrosating agent at elevated temperature (100° C.) to promote nitrosamine formation to a level high enough for analytical detection in a reasonable length of time. It has been reported that various amines could contain about 50 parts per billion of nitrosamine contaminant of unknown origin, but it is not analytically practical to study inhibitors with such low, although realistic, nitrosamine levels.

In the examples, studies of inhibition of nitrosamine formation involved testing of neat amine compositions at 100° C., with and without various amounts of inhibitors, with 0.1% (16 mMolar) sodium nitrite added. The concentration of nitrosamine in the test compositions was determined by liquid chromatography with UV detection.

The invention will become more clear when considered together with the following examples, which are set forth as being merely illustrative of the invention and which are not intended, in any manner, to be limitative thereof. Unless otherwise indicated, all parts and percentages are by weight.

EXAMPLE 1

Using six ounce, narrow mouth, glass bottles fitted with sealing caps, a number of tests were run with 100 grams of commercial grade triethanolamine in each of the bottles. Into two of the six ounce bottles were added 0.12 grams (8 mMolar) of 1,4-naphthohydroquinone, and then thoroughly mixed on a roller mill until all the material was dissolved. Into each test sample of amine was added 0.10 grams (16 mMolar) of sodium nitrite with thorough mixing (roller mill) until all of the sodium nitrite was dissolved.

Control samples (no inhibitor added) and the test samples containing naphthohydroquinone were placed in an oven at 100° C. with a cap loosely covering each bottle.

After a period of about 50 days at 100° C., analysis of each of the samples showed that the formation of nitrosamine contaminant (N-nitrosodiethanolamine) in the control samples was substantially greater (an average range of nitrosamine concentration in eight different samples of 360±25 ppm) than that found in the samples containing naphthohydroquinone (nitrosamine concentration of 60 ppm).

Analysis of samples was performed using the following procedure:

Samples to be analyzed are removed from the oven and placed in a dark cabinet for cooling to room temperature. After samples to be analyzed have been taken from the bottles, they are returned to the oven.

The samples are analyzed by a liquid chromatographic method employing a SPECTRA PHYSICS SP8000 Liquid Chromatograph having WATERS BONDAPAK C18 Column (300 mm×3.9 mm ID) with a 0.7 milliliter/min. mobile phase of 100% water. 50 microliters of a 5% solution of the sample in water is injected with N-Nitrosodiethanolamine detected in the ultraviolet at 234 nanometers.

EXAMPLE 2

The procedure of Example 1 was used to study the inhibition of nitrosamine formation in diethanolamine compositions containing 0.1% sodium nitrite with varying porportions of 1,4-naphthohydroquinone. For comparison purposes, samples containing no inhibitor and other samples containing varying proportions of hydroquinone, a compound suggested by Gray and Dugan, Jr., supra as a potential nitrosamine inhibitor in acidic aqueous media, were also used in this study. The type and proportions of inhibitor additive employed in the compositions of this Example and the amount of N-nitrosodiethanolamine contaminant formed after various periods of reacting at 100° C. are reported in Table I.

The data thus presented show that at 8 mMolar and 16 mMolar concentrations of additive, 1,4-naphthohydroquinone is considerably more effective than hydroquinone in inhibiting formation of nitrosamines, with both additives, however, affording very substantial inhibition of nitrosamines as compared to the control (no additive) samples. Surprisingly, the effectiveness of even very low concentrations (0.8 mMolar) of 1,4-naphthohydroquinone in preventing nitrosamine formation compared to the effectiveness of hydroquinone is readily apparent.

TABLE I

| Inhibitor Additive | Conc (mMolar) | Conc (parts per million) ppm | Day of Reaction at 100° C. in Diethanolamine with 0.1% Sodium Nitrite (16 mMolar) N-Nitrosodiethanolamine Formed (ppm) | | | | | | | | | | |
|---|---|---|---|---|---|---|---|---|---|---|---|---|---|
| | | | 1 | 2 | 11 | 13 | 20 | 21 | 22 | 53 | 55 | 56 | 67 |
| None | — | — | | 14 | | 364 | | | 506 | | 699 | | |
| None | — | — | | | 15 | 331 | | | 495 | | | 700 | |
| 1,4-Naphtho | 16 | 2280 | | | | | 35 | | 39 | 47 | | | |

TABLE I-continued

| Inhibitor Additive | Conc (mMolar) | Conc (parts per million) ppm | Day of Reaction at 100° C. in Diethanolamine with 0.1% Sodium Nitrite (16 mMolar) N-Nitrosodiethanolamine Formed (ppm) | | | | | | | | | | |
|---|---|---|---|---|---|---|---|---|---|---|---|---|---|
| | | | 1 | 2 | 11 | 13 | 20 | 21 | 22 | 53 | 55 | 56 | 67 |
| hydroquinone 1,4-Naphtho hydroquinone | 8 | 1140 | | | 34 | | 37 | | | 43 | | | |
| 1,4-Naphtho hydroquinone | 0.8 | 114 | | | 92 | | 91 | | | 90 | | | |
| 1,4-Naphtho hydroquine | 0.08 | 11.4 | | | 292 | | 448 | | | 551 | | | |
| Hydroquinone | 16 | 1600 | 11 | | | 89 | | 91 | | | | | 85 |
| Hydroquinone | 8 | 800 | 9 | | | 86 | | 86 | | | | | 86 |
| Hydroquinone | 0.8 | 80 | 6 | | | 255 | | 312 | | | | | 408 |
| Hydroquinone | 0.08 | 8 | 6 | | | 261 | | 364 | | | | | 616 |

EXAMPLE 3

The procedure of Example 1 was used to study the inhibition of nitrosamine formation in diethanolamine containing 0.1% sodium nitrite with a 8 mMolar concentration of inhibitor additives of 1,4-naphthohydroquinone and 1,4-naphthoquinone after different periods of time. A summary of the results obtained are presented in Table II, below.

TABLE II

| | N-Nitrosodiethanolamine Formed (ppm) Days at 100° C. | | |
|---|---|---|---|
| Additive | 6 | 29 | 46 |
| 1,4-Naphthoquinone (8 mMolar) | 29 | 31 | 32 |
| 1,4-Naphthohydroquinone (8 mMolar) | 27 | 30 | 29 |

EXAMPLE 4

Using the procedure of Example 1, the inhibition of nitrosamine formation in neat compositions of hexylamine, dioctylamine, ethylene diamine, piperidine, N-ethyl aniline, and tributyl amine, each of which compositions contain a 16 mMolar concentration of sodium nitrite and 8 mMolar concentration of 1,4-naphthohydroquinone are studied. In each case, the amount of nitrosamine contaminant after about 50 days at 100° C. is substantially lower than in compositions that do not contain said quinone additive.

What is claimed is:

1. Organic amine compositions which are substantially free from nitrosamine contaminants comprising an organic amine and a small inhibiting amount of an inhibiting additive which is a member selected from the group consisting of 1,4-naphthoquinone, 1,4-naphthohydroquinone, alkyl-substituted derivatives of said quinones, and mixtures of the same.

2. Organic amine compositions of claim 1 wherein said organic amine is selected from the group consisting of monoamines, polyamines, aromatic amines, and organic compounds which contain both amino and hydroxyl groups.

3. Organic amine compositions of claim 1 wherein said organic amine is an organic compound which contains both amino and hydroxyl group.

4. Organic amine compositions of claim 3 wherein said organic amine is an alkanolamine selected from the group consisting of monoethanolamine, diethanolamine, triethanolamine, and mixtures of the same.

5. Organic amine compositions of claim 1 comprising at least about 1 per million of said quinone inhibitor.

6. Organic amine compositions of claim 3 comprising at least about 1 part per million of said quinone inhibitor.

7. Organic amine compositions of claim 1 wherein said inhibiting additive is 1,4-naphthoquinone or 1,4-naphthohydroquinone.

8. Organic amine compositions of claim 3 wherein said inhibiting additive is 1,4-naphthoquinone or 1,4-naphthohydroquinone.

9. Organic amine compositions of claim 1 wherein said inhibiting additive is dissolved in said organic amine.

10. Organic amine compositions of claim 1 which are aqueous solutions thereof.

11. A method for reducing the formation of nitrosamine contaminants in compositions containing organic amines which comprises combining an inhibiting amount of an inhibiting additive which is a member selected from the group consisting of 1,4-napthoquinone, 1,4-naphthohydroquinone, alkyl-substituted derivatives of said quinones, and mixtures of the same with said compositions.

12. The method of claim 11 wherein said organic amine compositions is an organic amine selected from the group consisting of monoamines, polyamines, aromatic amines, and organic compounds which contain both amino and hydroxyl groups.

13. The method of claim 11 wherein said organic amine composition is an alkanolamine.

* * * * *